(12) United States Patent
Hayashi et al.

(10) Patent No.: US 6,489,269 B1
(45) Date of Patent: Dec. 3, 2002

(54) PLANT-ACTIVATING AGENT

(75) Inventors: Masaharu Hayashi, Wakayama (JP);
Tadayuki Suzuki, Wakayama (JP);
Masatoshi Kamei, Wakayama (JP);
Toshio Hayashi, Wakayama (JP);
Kazuhiko Kurita, Wakayama (JP)

(73) Assignee: Kao Corporation, Tokyo (JP)

(*) Notice: Subject to any disclaimer, the term of this patent is extended or adjusted under 35 U.S.C. 154(b) by 0 days.

(21) Appl. No.: 09/434,174

(22) Filed: Nov. 5, 1999

(30) Foreign Application Priority Data

Nov. 6, 1998 (JP) .......................................... 10-315737

(51) Int. Cl.⁷ ............................................... A01N 31/00
(52) U.S. Cl. ....................................................... 504/353
(58) Field of Search ......................................... 504/353

(56) References Cited

U.S. PATENT DOCUMENTS

| | | | |
|---|---|---|---|
| 3,900,307 A | 8/1975 | Abramitis | 71/78 |
| 3,922,977 A * | 12/1975 | Lavo et al. | 111/1 |
| 4,169,716 A * | 10/1979 | Ashmead | 71/77 |
| 4,190,427 A | 2/1980 | Ravallo | 71/29 |
| 5,385,750 A | 1/1995 | Aleksejczyk et al. | |
| 5,693,592 A | 12/1997 | Illingworth | 504/118 E |

FOREIGN PATENT DOCUMENTS

| | | | |
|---|---|---|---|
| CN | 1137861 A | | 12/1996 |
| EP | 0161395 A2 | | 11/1985 |
| EP | 313255 | * | 4/1989 |
| GB | 1327092 | | 8/1973 |
| GB | 1327092 A | | 8/1973 |
| GB | 1574938 | | 9/1977 |
| JP | 5540674 A | | 3/1980 |
| JP | 6136188 A | | 2/1986 |
| JP | 1141526 A | | 6/1989 |
| JP | 1157492 A | | 6/1989 |
| JP | 9100207 | * | 4/1997 |
| JP | 09322647 A | | 12/1997 |
| WO | 9851148 A1 | | 11/1998 |

OTHER PUBLICATIONS

Handbook of Agricultural Chemicals, edited in 1994, p. 475.

* cited by examiner

*Primary Examiner*—Alton Pryor
(74) *Attorney, Agent, or Firm*—Birch, Stewart, Kolasch & Birch, LLP

(57) ABSTRACT

The present invention provides a plant-activating agent which effects no chemical injury on plant and which makes an activity of plant improve efficiently. That is to say, the present invention provides a method of activating a plant, which comprises treating the plant with a mono-alcohol having 12 to 24 carbon atoms as a plant-activating agent; use of the mono-alcohol as a plant-activating agent; and a plant-activating agent or composition comprising the mono-alcohol; optionally with a surfactant, a fertilizer component and/or a chelating agent.

30 Claims, No Drawings

PLANT-ACTIVATING AGENT

TECHNICAL FIELD

The present invention relates to a plant-activating agent and/or a plant-activating composition. Also, as use thereof, the present invention provides a method of activating a plant by applying thereof in the state of r solution or solid to a root, stem, phylloplane or fruit of plant, such as spraying onto phylloplanes and irrigating into soil. Now, hereinafter, the term of "plant" includes plants, vegetables, fruits, crops, seeds, flowers, herbs, floras, and so on.

BACKGROUND ART

Various nutrient elements are necessary for growth of plants. It is known that lack of some of the elements causes the hindrance of the growth of the plants. For example, the big three fertilizer components function as follows. Nitrogen is a component element of proteins, and phosphorus is a formation element of nucleic acid or phosphorus lipid and further plays an important part in energy metabolism and synthetic or decomposing reaction of a substance. Potassium has a physiological action of substance metabolism or substance migration. If these main components lacks, the growth of plants generally becomes poor. Calcium is an important component constituting the plant-realities and cells, and further plays an important part in maintenance of the balance of the metabolic system. The lacking state of calcium causes physiological troubles. Besides, various nutrients as follows are necessary for plants: Mg, Fe, S, B, Mn, Cu, Zn, Mo, Cl, Si, Na and the like.

Nutritious components such as nitrogen, phosphorus and potassium are applied as basal fertilizer or additional fertilizer. Alternatively, they are applied by diluting liquid fertilizer and irrigating the diluted fertilizer into soil or by spraying the diluted fertilizer onto phylloplanes. These fertilizers are necessary and/or essential for the growth of plants. However, even if they are applied at larger concentrations than some values, the growth of plants and the yield of the plants cannot be further improved.

However, it is an important theme in agricultural production to promote the growth of agricultural plants and increase the yield per unit area to strive for an increase in income. Various plant growth regulators being necessary for this have been developed and used. The plant growth regulators, the typical examples of which include gibberellin and auxin, are used to regulate growth reaction or form-producing reaction such as germination, rooting, expansion, flowering and bearing. The actions of these substances are many-sided or complicated. The uses thereof are restrictive.

In order to solve such problems, there are known a phylloplane spraying agent using an oligosaccharide (JP-A 9-322647), and techniques in which a liquid fertilizer comprising a sugar, a mineral, an amino acid, an extract from seaweeds, or a fermentation extract of microorganisms is sprayed onto phylloplanes or is applied in the form of the liquid. In the present situation, however, their effects are insufficient for practical use.

For an increased yield, when a large amount of fertilizer is applied into the soil, various components may become excessive in the soil so that the balance of absorption thereof may become bad or the growth of plants may be delayed. As a result, there arise, for example, problems that the increased yield, as an aim, cannot be attained or the quality such as sugar concentration (Brix. value) or freshness (green degree) does not rise. And then, since there are a limit of absorption from roots which aim absorption of nutrients, direct absorption of necessary fertilizer elements from phylloplanes or fruits is attempted by spraying an aqueous solution or aqueous suspension of the elements. However, even if the aqueous solution of the necessary elements is merely sprayed onto phylloplanes, a problem arises from the viewpoint of absorption efficency. Spraying excessive amounts of fertilizer elements impose stress on plants, resulting chemical injury.

Handbook of Agricultural Chemicals (edited in 1994) on page 475, discloses decyl alcohol as a restrainer of an axillary bud of a tobacco-plant. JP-A 55-40674 discloses an alcohol having 30 carbon atoms as a plant growth promoter.

It is known to dilute a foam concentrated product with water, generate foams at a static pressure of 15 psi or more in a foam generator connected to a tap water pipe, and treat plants or soil with the resultant foams (U.S. Pat. No. 3,922,977). However, this patent never discloses nor suggests use as a plant-activating agent or a method for activating plants.

DISCLOSURE OF THE INVENTION

The present invention relates to a plant-activating agent comprising a mono-alcohol having 12–24 carbon atoms and relates to a plant-activating composition comprising the mono-alcohol, and a surfactant, a fertilizer component or a chelating agent.

Namely, the present invention provides a plant-activating agent comprising a mono-alcohol having 12–24 carbon atoms, and provides a plant-activating composition comprising the mono-alcohol and at least one compound selected from a surfactant and a chelating agent.

The invention provides a method of activating a plant, which comprises treating the plant with a mono-alcohol having 12 to 24 carbon atoms as a plant-activating agent; and use of the mono-alcohol as a plant-activating agent.

It is preferred that the plant is treated further with at least one compound selected from a surfactant, a fertilizer component and a chelating agent, in use or method of the above-mentioned.

The surfactant may be selected from an ester group-containing nonionic surfactant, an ether group-containing nonionic surfactant having no nitrogen atom, an amphoteric surfactant, a carboxylic anionic surfactant and a phosphoric anionic surfactant, in use or method of the above-mentioned.

The invention provides a plant-activating composition comprising a mono-alcohol having 12 to 24 carbon atoms and one group selected from (i) a chelating agent, (ii) a surfactant and a chelating agent, (iii) a fertilizer component and a chelating agent, and (iv) a surfactant, a fertilizer component and a chelating agent.

Another composition may preferably comprise a mono-alcohol having 12 to 24 carbon atoms and at least one surfactant selected from an ester group-containing nonionic surfactant, a ether group-containing nonionic surfactant having no nitrogen atom, an amphoteric surfactant, a carboxylic anionic surfactant and a phosphoric anionic surfactant.

A plant-activating composition of the invention comprises a mono-alcohol having 12 to 24 carbon atoms and at least one surfactant selected from an ester group-containing nonionic surfactant, an ether group-containing nonionic surfactant having no nitrogen atom, an amphoteric surfactant, a carboxylic anionic surfactant and a phosphoric anionic surfactant, optionally further comprising a fertilizer component.

A plant-activating composition of the invention comprises a mono-alcohol having 12 to 24 carbon atoms and one group selected from (iii) a fertilizer component and a chelating agent, (iv) a surfactant, a fertilizer component and a chelating agent and (v) a surfactant and a fertilizer component.

MODES FOR CARRYING OUT THE INVENTION

In the present invention, a mono-alcohol having 12–24 carbon atoms, preferably 14–22 carbon atoms, particularly preferably 16–20 carbon atoms, is used since the alcohol can effectively give plant vital power activation without causing chemical injury. The hydrocarbon group of the mono-alcohol may be saturated or unsaturated, and may be in the form of a straight chain, a branched chain or a cyclic chain. The hydrocarbon group is preferably an alkyl group being a straight or branched chain, particularly preferably an alkyl group being a straight chain. Specific examples of the mono-alcohol include lauryl alcohol, cetyl alcohol, stearyl alcohol, eicosanol, behenyl alcohol, phytol, oleyl alcohol, and alcohols originated from natural fats and/or oils.

The form of the plant-activating agent comprising the mono-alcohol according to the present invention may be any form, such as a liquid, a flowable, a paste, a wettable powder, a granule, a dust formulation or a tablet. At the time of use, the plant-activating agent is generally sprayed in the form of an aqueous solution, an aqueous dispersion, or an aqueous emulsion which has a mono-alcohol concentration of from 1 to 500 ppm onto phylloplanes or roots of a plant.

In order to supply the plant-activating agent of the present invention to a plant, various methods may be used. Examples of the methods include a method of applying a dust formation or a granule as fertilizer directly, a method of spraying a diluted aqueous solution. directly onto phylloplanes, stems or fruits of a plant, a method of injecting a diluted aqueous solution into soil, and a method of supplying to dilute and to mix into a liquid for a hydroponics and a supplying water which are contacted with roots and which are such as a hydroponics and a rock wool.

Plants, which can be treated with the plant-activating agent of the present invention, may be a fruit vegetable such as a cucumber, a pumpkin, a watermelon-plant, a melon, a tomato, an eggplant, a green pepper, a strawberry, an okra, kidney beans in a pod, a broad bean, a pea, green soybeans in a pod and a corn; a leaf vegetables such as a Chinese cabbage, greens for pickling, a Brassica campestris (a Chinese spinach-like green vegetable), a cabbage, a cauliflower, a broccoli, a Brussels sprout, an onion, a Welsh onion, a garlic, a scallion, a leek, an asparagus, a lettuce, a green for salad (which is called Saladana in Japan), a celery, a spinach, a crown daisy, a parsley, a trefoil (which is called Mitsuba in Japan and is useful as herb), a dropwort, an udo (which is an Aralia cordata), a Japanese ginger, a Japanese butterbur and a labiate; and a root vegetable such as a radish, a turnip, a burdock, a carrot, a potato, a taro, a sweet potato, a yam, a ginger-plant (which is called Shoga in Japan) and a lotus root. Besides, the plant-activating agent may be used for a rice-plant; a barley, a wheat or a group thereof; petalous-plants and the like.

In the present invention, the following surfactant is preferably used together with the above-mentioned mono-alcohol to promote emulsification, dispersion, solubilization and permeation of the mono-alcohol.

Examples of nonionic surfactants include sorbitan fatty acid esters, polyoxyalkylene sorbitan fatty acid esters, polyoxyalkylene fatty acid esters, glycerol fatty acid esters, polyoxyalkylene glycerol fatty acid esters, polyglycerol fatty acid esters, polyoxyalkylene polyglycerol fatty acid esters, sucrose fatty acid esters, resin acid esters, polyoxyalkylene resin acid esters, polyoxyalkylene alkyl ethers, polyoxyalkylene alkylphenyl ethers, alkyl(poly)glycosides and polyoxyalkylenealkyl(poly)glycosides. Preferably, an ether group-containing nonionic surfactant having no nitrogen atom and ester group-containing nonionic surfactant may be cited.

Examples of anionic surfactants include carboxylic, sulfonic, sulfuric ester group-containing and phosphoric ester group-containing surfactants, and a carboxylic and phosphoric ester group-containing surfactants are preferred.

Examples of the carboxylic surfactants include fatty acids having 6–30 carbon atoms or salts thereof, polyhydric carboxylic acid salts, polyoxyalkylene alkyl ether carboxylic acid salts, polyoxyalkylene alkylamide ether carboxylic acid salts, rhodinic acid salts, dimmer acid salts, polymer acid salts and tall oil fatty acid salts.

Examples of the sulfonic surfactants include alkylbenezenesulfonic acid salts, alkylsulfonic acid salts, alkylnaphthalenesulfonic acid salts, naphthalenesulfonic acid salts, diphenyl ether sulfonic acid salts, condensates of alkylnaphthalenesulfonic acid, and condensate of naphthalenesulfonic acid.

Examples of the sulfuric ester group-containing surfactants include alkylsulfuric ester salts (alkylsulfuric acid salts), polyoxyalkylene alkylsulfuric ester salts (polyoxyalkylene alkylsulfuric acid salts), polyoxyalkylene alkyl phenyl ether sulfuric acid salts, tristyrenatedphenol sulfuric acidester salts, polyoxyalkylene distyrenated phenol sulfuric acid ester salts and alkylpolyglycoside sulfuric acid salts.

Examples of phosphoric acid ester group-containing surfactants include alkyl phosphoric acid ester salts, alkylphenylphosphoric acid ester salts, polyoxyalkylene alkylphosphoric acid ester salts and polyoxyalkylene alkylpheneylphosphoric acid ester salts.

Examples of the salts include metallic salts (such as salts of Na, K, Ca, Mg and Zn), ammonium salts, alkanol amine salts and aliphatic amine salts.

Examples of amphoteric surfactants include amino acid group-containing, betaine group-containing, imidazoline group-containing and amine oxide group-containing surfactants.

Examples of the amino acid group-containing surfactants include acylamino acid salts, acylsarcosine acid salts, acyloylmethylaminopropionic acid salts, alkylaminopropionic acid salts and acylamide ethylhydroxyethylmethylcarboxylic acid salts.

Examples of the betaine group-containing surfactants include alkyldimethylbetaine, alkylhydroxyethylbetaine, acylamide propylhydroxypropylammonia sulfobetaine, acylamide propylhydroxypropylammonia sulfobetaine and ricinoleic acid amide propyl dimethylcarboxy methylammonia betaine.

Examples of the imidazoline group-containing surfactants include alkylcarboxy methylhydroxy ethylimidazolinium betaine and alkylethoxy carboxy methylimidazolinium betaine.

Examples of the amine oxide group-containing surfactants include alkyldimethylamine oxide, alkyldiethanolamine oxide and alkylamidepropylamine oxide.

One kind of the above-mentioned surfactants may be used, and a mixture of two or more kinds of the above-mentioned surfactants may be used. In the case that one of these surfactants comprises a polyoxyalkylene group, the polyoxyalkylene group is preferably a polyoxyethylene group and the average mole number of added polyoxyethylene groups is preferably from 1 to 50.

As the surfactant, at least one compound selected from ester group-containing nonionic surfactants, ether group-containing nonionic surfactants having no nitrogen atom, amphoteric surfactants, carboxylic anionic surfactants and phosphoric anionic surfactant is preferable.

In particular, it is preferable to be at least one compound selected from ester group-containing nonionic surfactants and ether group-containing nonionic surfactants having no nitrogen atom.

The following fertilizer components may be used together with the above-mentioned mono-alcohol. Specific examples thereof may be inorganic or organic compounds which can supply elements such as N, P, K, Ca, Mg, S, B, Fe, Mn, Cu, Zn, Mo, Cl, Si and Na, in particular N, P, X, Ca and Mg. Examples of such inorganic compounds include ammonium nitrate, potassium nitrate, ammonium sulfate, ammonium chloride, ammonium phosphate, sodium nitrate, urea, ammonium carbonate. potassium phosphate, calcium superphosphate, fused phosphate fertilizer ($3MgO \cdot CaO \cdot P_2O_5 \cdot 3CaSiO_2$), potassium sulfate, potassium chloride, nitrate of lime, slaked lime, carbonate of lime, magnesium sulfate, magnesium hydroxide and magnesium carbonate. Examples of the organic compounds include fowl droppings, cow dung, Bark compost, amino acid, peptone, amino acid solution (which is called Mieki in Japan), fermentation extracts, calcium salts of organic acids (such as citric acid, gluconic acid and succinic acid), and calcium salts of fatty acids (such as formic acid, acetic acid, propionic acid, caprylic acid, capric acid and caproic acid). These fertilizer components may be used together with the surfactant. In the case that fertilizer components are sufficiently applied as basal fertilizer to soil as seen in outdoor cultivation of a rice-plant or vegetables, it is unnecessary to mix the fertilizer components. Further, when a cultivation form is such as a fertigation (a hydroponic soil culture) or a hydroponics, when it avoids applying excessively basal fertilizer and when it is a type of providing a fertilizer component as well as irrigation-water, the fertilizer component is preferably mixed.

When the plant-activating composition of the present invention is mixed with the following organic acid having chelating ability or a salt thereof, the growth and absorption efficiency of fertilizer improved further. Specific examples thereof include oxycarboxylic acids such as citric acid, gluconic acid, malic acid, heptonic acid, oxalic acid, malonic acid, lactic acid, tartaric acid, succinic acid, fumaric acid, maleic acid, adipic acid and glutaric acid; polyhydric carboxylic acids; and salts thereof such as potassium salt, sodium salt, alkanolamine salt and aliphatic amine salt.

Mixing a chelating agent besides the organic acids also causes the growth and absorption efficiency of fertilizer to be improved. Examples of the mixed chelating agents include aminocarboxylic group-containing chelating agents such as EDTA, NTA and CDTA.

The form, spraying method and the like of plant-activating composition of the present invention are the same as described above. If necessary, water and/or a solvent may be added to the composition.

In the plant-activating composition or the fertilizer composition of the present invention, it is preferable to use respectively; per 100 parts by weight of the mono-alcohol; 10–20000 parts, in particular 100–2000 parts, by weight of the surfactant; 0–50000 parts, in particular 10–5000 parts, by weight of the fertilizer component; 0–1000 parts, in particular 10–500 parts, by weight of the chelating agent; and 0–5000 parts, in particular 10–500 parts, by weight of other nutritious sources (such as sugars, amino acids and vitamins).

In the case that the plant-activating composition is applied in the form of a dust formulation or granule as fertilizer to soil, it is preferable that the used dust formulation or granule comprise the above-mentioned components except water at the same ratios as above, in general. This dust formulation or granule may comprise a vehicle to prevent caking.

The plant-activating agent of the present invention makes it possible to improve the activity of plant effectively without causing any chemical injury on plants if the plants are treated with an appropriate concentration of the plant-activating agent. For this reason, it can be used for various plants. According to the present invention, promotion of taking root of a plant, increase of chlorophyll value (SPAD value), increase of absorption efficiency of fertilizer and so on are seen as improvement at growth of plant.

EXAMPLES

Example 1

<Test of Soil-treatment for Tomato Seedlings>

Species: "Home Momotaro" (Takii & Company LTD)

Vessel for cultivation: a cell tray having 50 holes for germination, and a pot (diameter: 14 cm) for cultivation Used soil: Takii soil for seeding [$N:P_2O_5:K_2O$= 480:750:345 (mg/L), pH 6.4, and EC: 0.96]

Under the above-mentioned conditions, seeds were sown in the cell tray having 50 holes. When 2 weeks went by after germination, the plants were transplanted to the pot. At intervals of 1 week after 3 days from the transplantation, the soil was treated 4 times with fertilizer compositions being blended raw materials shown in Table 1 and 1000 ppm of a fertilizer component "Otsuka OKF2" (made by Otsuka Chemical Co., Ltd.). The concentrations of the blended raw materials are shown in Table 1 and their balance was water. The amount for each of the treatments was about 50 ml per pot. The fertilizer compositions were caused to penetrate into the soils. For the respective compositions, the test was repeated 3 times. On the 7th day after the fourth treatment, the growth state [height and weight („hereinafter, "weight" means raw-weight,] of the respective plants and the SPAD value (SPAD 502 made by Minolta Co., Ltd.) representing a green degree were measured. The measured values obtained from the 3 repetitions were averaged. The averaged value was relatively compared as the value that was obtained from the no-treated area (Comparative product 1–4) and made to be 100. The results are shown in Table 1.

TABLE 1

| No. | Blended raw materials | Concentration (ppm) | Height | Weight | SPAD value |
|---|---|---|---|---|---|
| Invention product | | | | | |
| 1-1 | Stearyl alcohol | 100 | 148 | 142 | 122 |
|  | POE(20) sorbitan monooleate | 500 | | | |
| 1-2 | Eicosanol | 200 | 145 | 140 | 119 |
|  | POE(20) hardened castor oil | 1000 | | | |
| 1-3 | Decyldodecanol | 100 | 134 | 124 | 110 |
|  | POE(15) glycerol beef tallow fatty acid ester | 500 | | | |
| 1-4 | Lauryl alcohol | 50 | 132 | 122 | 112 |
|  | Na salt of POE(3) lauryl sulfuric ester | 100 | | | |
|  | POE(20) sorbitan monolaurate | 200 | | | |
| 1-5 | Oleyl alcohol | 300 | 138 | 130 | 118 |
|  | POE(20) sorbitan monolaurate | 600 | | | |
|  | Sorbitan monolaurate | 400 | | | |
| 1-6 | Stearyl alcohol | 200 | 144 | 138 | 122 |
|  | Cetyl alcohol | 100 | | | |
|  | POE(20) sorbitan monolaurate | 500 | | | |
|  | Tetraglycerol monooleate | 500 | | | |
| 1-7 | Branched $C_{12}/C_{13}$ alcohol* | 100 | 118 | 110 | 112 |
|  | POE(10) oleic acid ester | 500 | | | |
|  | Alkylglucoside** | 200 | | | |
| 1-8 | $C_{16}/C_{18}$ alcohol (weight ratio = 3/7. This is true hereinafter.) | 200 | 158 | 144 | 120 |
|  | POE(20) sorbitan monooleate | 200 | | | |
|  | Sucrose stearic acid ester | 300 | | | |
| 1-9 | Stearyl alcohol | 50 | 156 | 147 | 129 |
|  | POE(20) sorbitan monooleate | 200 | | | |
|  | EDTA.4Na | 20 | | | |
| 1-10 | Coconut alcohol ($C_{14}/C_{16}/C_{18}$ = 10/70/20) | 100 | 122 | 124 | 118 |
|  | Oleic acid monodiglyceride | 200 | | | |
|  | POE(20) sorbitan monooleate | 500 | | | |
| Comparative product | | | | | |
| 1-1 | Ethanol | 200 | 95 | 98 | 99 |
|  | POE(20) sorbitan monooleate | 200 | | | |
| 1-2 | Isopropanol | 100 | 86 | 98 | 88 |
|  | Na salt of POE(3) lauryl sulfuric ester | 100 | | | |
|  | POE(20) sorbitan monolaurate | 200 | | | |
| 1-3 | Octyl alcohol | 100 | 75 | 88 | 86 |
|  | POE(20) sorbitan monolaurate | 200 | | | |
| 1-4 | Water (no-treated area) | — | 100 | 100 | 100 |

*Synthetic $C_{12}/C_{13}$ alcohol (branch ratio = 30%. This is true hereinafter.)
**Alkyl($C_{10}/C_{12}/C_{14}$ = 60/30/10) polyglucoside (Notes) In Table 1, polyoxyethylene is abbreviated to POE, the respective numbers inside parentheses are the average mole numbers of added ethylene oxide (,the hereinafter is the same as this). Also, for example, notes of $C_{16}$ and $C_{18}$ mean the number of carbon atoms being 16 and 18, respectively (,the hereinafter is the same as this).

From the results shown in Table 1, it is noted that the plant-activating composition of the present invention made the growth of the plants promote remarkably and the green degree raise obviously, compared with comparative products.

Example 2

<Test of Soil-treatment for Brassica campestris Seedlings>
Brassica campestris seeds: Takii & Company LTD
Vessel for cultivation: a cell tray having 50 holes
Used soil: Takii soil for seeding (,which was the same as in Example 1)

Under the above-mentioned conditions, seeds were sown in the cell tray having 50 holes. At intervals of 1 week after 2 weeks from germination, the soil was treated 4 times with fertilizer compositions being blended raw materials shown in Table 2 and 1000 ppm of a fertilizer component "Otsuka OKF2". The concentrations of the blended raw materials are shown in Table 2 and their balance was water. The amount for each of the treatments was about 60 ml for respective 10 holes. The fertilizer compositions were caused to penetrate into the soils. For the respective compositions, the test for 10 holes was performed 3 times, i.e. 3 repetitions. On the 7th day after the fourth treatment, the growth state (height and weight) of the respective plants and the SPAD value (SPAD 502 made by Minolta Co., Ltd.) representing a green degree were measured. The measured values obtained from the 3 repetitions were averaged. The averaged value was relatively compared as the value that was obtained from the no-treated area (Comparative product 2–4) and was made to be 100. The results are shown in Table 2.

TABLE 2

| No. | Blended raw materials | Concentration (ppm) | Height | Weight | SPAD value |
|---|---|---|---|---|---|
| Invention product | | | | | |
| 2-1 | Lauryl alcohol | 100 | 142 | 138 | 110 |
| | POE(20) sorbitan monooleate | 200 | | | |
| 2-2 | Myristyl alcohol | 100 | 148 | 140 | 114 |
| | POE(20) sorbitan monooleate | 200 | | | |
| 2-3 | Cetyl alcohol | 100 | 158 | 144 | 114 |
| | POE(20) sorbitan monooleate | 200 | | | |
| 2-4 | Stearyl alcohol | 100 | 160 | 152 | 140 |
| | POE(20) sorbitan monooleate | 200 | | | |
| 2-5 | Oleyl alcohol | 100 | 152 | 160 | 138 |
| | POE(20) sorbitan monooleate | 200 | | | |
| 2-6 | Eicosanol | 100 | 140 | 138 | 120 |
| | POE(20) sorbitan monooleate | 200 | | | |
| 2-7 | Behenyl alcohol | 100 | 132 | 142 | 118 |
| | POE(20) sorbitan monooleate | 200 | | | |
| 2-8 | Phytol | 100 | 142 | 146 | 110 |
| | POE(20) sorbitan monooleate | 200 | | | |
| 2-9 | $C_{16}/C_{18}$ alcohol ($C_{16}/C_{18}$ = 3/7) | 100 | 156 | 162 | 136 |
| | POE(20) sorbitan monooleate | 200 | | | |
| 2-10 | $C_{16}/C_{18}$ alcohol ($C_{16}/C_{18}$ = 3/7) | 100 | 168 | 176 | 136 |
| | POE(20) sorbitan monooleate | 200 | | | |
| | Heptononic acid Na salt | 20 | | | |
| 2-11 | $C_{16}/C_{18}$ alcohol ($C_{16}/C_{18}$ = 3/7) | 100 | 166 | 176 | 132 |
| | POE(20) sorbitan monooleate | 200 | | | |
| | Malonic acid | 20 | | | |
| 2-12 | $C_{16}/C_{18}$ alcohol ($C_{16}/C_{18}$ = 3/7) | 100 | 172 | 172 | 130 |
| | POE(20) sorbitan monooleate | 200 | | | |
| | Maleic acid | 20 | | | |
| 2-13 | Branched $C_{12}/C_{13}$ alcohol | 100 | 136 | 148 | 112 |
| | POE(20) sorbitan monooleate | 200 | | | |
| | EDTA.4Na | 20 | | | |
| 2-14 | coconut alcohol ($C_{14}/C_{16}/C_{18}$ = 10/70/20) | 100 | 146 | 156 | 118 |
| | POE(20) sorbitan monooleate | 200 | | | |
| | EDTA.4Na | 20 | | | |
| Comparative product | | | | | |
| 2-1 | Ethanol | 100 | 96 | 86 | 90 |
| | POE(20) sorbitan monooleate | 200 | | | |
| | Octyl alcohol | 100 | | | |
| 2-2 | Octyl alcohol | 100 | 74 | 68 | 88 |
| | POE(20) sorbitan monooleate | 200 | | | |
| 2-3 | Decyl alcohol | 100 | 82 | 76 | 88 |
| | POE(20) sorbitan monooleate | 200 | | | |
| 2-4 | Water (no-treated area) | — | 100 | 100 | 100 |

Example 3
<Test of Phylloplane-treatment for Rice-plant Seedlings>
Species: Kinuhikari
Vessel for cultivation: a cell tray having 50 holes
Used soil: Ryujou Iseki Baido (seedling soil for rice-plant) (N:P:K=1:1:1) (made by Iseki & Company, LTD)

Under the above-mentioned conditions, seeds were sown in the cell tray having 50 holes. After the plants geminated, the plants fell in the dark age followed by the virescent age. At a period when the height of the plants became about 3 cm (after 3 days), the phylloplanes were treated 1 time with fertilizer compositions being blended raw materials shown in Table 3 and 1000 ppm of a fertilizer component "Otsuka OKF2". The concentrations of the blended raw materials are shown in Table 3 and their balance was water. The amount for each of the treatments was about 1 L per 50 holes. At the 3.2 leaf age, which was final during the raising seedling period, the growth state (height, weight, weight of the portion on the ground and weight of the portion under the ground) of the respective plants and the SPAD value (SPAD 502 made by Minolta Co., Ltd.) representing a green degree of a leaf were measured. The measured value was relatively compared as the value that was obtained from the no-treated area (Comparative product 3–4) and made to be 100. The results are shown in Table 3.

TABLE 3

| No. | Blended raw materials | Concentration (ppm) | Height n = 20 | weight of the portion on the ground n = 20 | weight of the portion under the ground n = 20 | SPAD value n = 20 |
|---|---|---|---|---|---|---|
| Invention product | | | | | | |
| 3-1 | Cetyl alcohol<br>POE(20) sorbitan monooleate | 10<br>50 | 140 | 106 | 112 | 110 |
| 3-2 | Cetyl alcohol<br>POE(20) sorbitan monooleate | 50<br>250 | 144 | 108 | 116 | 114 |
| 3-3 | Cetyl alcohol<br>POE(20) sorbitan monooleate | 100<br>500 | 152 | 114 | 120 | 120 |
| 3-4 | Cetyl alcohol<br>POE(20) sorbitan monooleate | 500<br>1000 | 156 | 116 | 130 | 128 |
| 3-5 | Stearyl alcohol<br>POE(20) sorbitan monooleate | 10<br>50 | 138 | 108 | 120 | 116 |
| 3-6 | Stearyl alcohol<br>POE(20) sorbitan monooleate | 50<br>250 | 142 | 110 | 124 | 120 |
| 3-7 | Stearyl alcohol<br>POE(20) sorbitan monooleate | 100<br>500 | 156 | 118 | 130 | 122 |
| 3-8 | Stearyl alcohol<br>POE(20) sorbitan monooleate | 500<br>1000 | 162 | 120 | 133 | 136 |
| 3-9 | $C_{16}/C_{18}$ alcohol ($C_{16}/C_{18}$ = 3/7)<br>POE(20) sorbitan monooleate | 10<br>50 | 136 | 106 | 118 | 136 |
| 3-10 | $C_{16}/C_{18}$ alcohol ($C_{16}/C_{18}$ = 3/7)<br>POE(20) sorbitan monooleate | 50<br>250 | 136 | 110 | 122 | 136 |
| 3-11 | $C_{16}/C_{18}$ alcohol ($C_{16}/C_{18}$ = 3/7)<br>POE(20) sorbitan monooleate | 100<br>500 | 142 | 112 | 128 | 132 |
| 3-12 | $C_{16}/C_{18}$ alcohol ($C_{16}/C_{18}$ = 3/7)<br>POE(20) sorbitan monooleate | 500<br>1000 | 148 | 116 | 130 | 130 |
| Comparative product | | | | | | |
| 3-1 | Octyl alcohol<br>POE(20) sorbitan monooleate | 10<br>50 | 90 | 92 | 96 | 86 |
| 3-2 | Octyl alcohol<br>POE(20) sorbitan monooleate | 50<br>250 | 88 | 80 | 74 | 76 |
| 3-3 | Octyl alcohol<br>POE(20) sorbitan monooleate | 100<br>500 | 68 | 72 | 62 | 66 |
| 3-4 | Water (no-treated area) | — | 100 | 100 | 100 | 100 |

Example 4

<Test of Reproductive Ability Using Chlorella Cells>

Chlorella cells, which are green cells of a higher plant, were cultured with vibration in an inorganic-salt medium. Raw materials shown in Table 4 were added thereto, and then reproductive ability of chlorella cells (ability for increasing the number of the cells) was evaluated by comparison with the result obtained from a medium which was no-treated (i.e., only original nutrients of the inorganic salt medium). For the respective compositions, the test was repeated 3 times. The concentration of the cells was set to $1.00 \times 10^5$ cells (per ml) at the start of the test. The numbers of the chlorella cells after 10 days from the addition of the various raw materials followed by culture of the cells are shown as the relative values compared with the value that was obtained from the medium which was no-treated (Comparative product 4–9) and made to be 100. The results are shown in Table 4. As the inorganic salt medium, a Linsmaier-Skoog (LS) medium was used.

TABLE 4

| Test No. | Blended raw materials | Concentration (ppm) | Result of the test proliferating ability of cells |
|---|---|---|---|
| Invention product | | | |
| 4-1 | Lauryl alcohol | 10 | 115 |
| 4-2 | Myristyl alcohol | 10 | 128 |
| 4-3 | Myristyl alcohol<br>Stearyl alcohol | 5<br>5 | 138 |
| 4-4 | Cetyl alcohol | 10 | 148 |
| 4-5 | Cetyl alcohol<br>Stearyl alcohol | 5<br>5 | 160 |
| 4-6 | Stearyl alcohol | 10 | 168 |
| 4-7 | Oleyl alcohol | 10 | 154 |
| 4-8 | Eicosanol | 10 | 152 |
| 4-9 | Docosanol | 10 | 130 |
| 4-10 | Tetracosanol | 10 | 122 |
| 4-11 | Lauryl alcohol<br>Malonic acid | 10<br>4 | 119 |

TABLE 4-continued

| Test No. | Blended raw materials | Concentration (ppm) | Result of the test proliferating ability of cells |
|---|---|---|---|
| 4-12 | Cetyl alcohol | 10 | 152 |
|  | Ascorbic acid Na salt | 4 |  |
| 4-13 | Stearyl alcohol | 10 | 172 |
|  | EDTA.4Na | 4 |  |
| 4-14 | Eicosanol | 10 | 160 |
|  | EDTA.4Na | 4 |  |
| 4-15 | Cetyl alcohol | 30 | 142 |
| 4-16 | Stearyl alcohol | 30 | 156 |
| 4-17 | Eicosanol | 30 | 146 |
| 4-18 | Cetyl alcohol | 30 | 146 |
|  | Ascorbic acid Na salt | 30 |  |
| 4-19 | Stearyl alcohol | 30 | 159 |
|  | EDTA.4Na | 15 |  |
| 4-20 | Eicosanol | 30 | 150 |
|  | EDTA.4Na | 15 |  |
| 4-21 | Tetracosanol | 10 | 128 |
|  | Fumaric acid | 4 |  |
| Comparative product | | | |
| 4-1 | Propanol | 10 | 96 |
| 4-2 | Hexanol | 10 | 93 |
| 4-3 | Propanol | 5 | 92 |
|  | Octanol | 5 |  |
| 4-4 | Decyl alcohol | 10 | 91 |
| 4-5 | Decyl alcohol | 10 | 94 |
|  | Fumaric acid | 4 |  |
| 4-6 | Hexanol | 5 | 96 |
|  | Ethanol | 5 |  |
| 4-7 | Octanol | 30 | 95 |
| 4-8 | Propanol | 10 | 98 |
|  | EDTA.4Na | 4 |  |
| 4-9 | Inorganic salt medium (no-treated area) | — | 100 |

Example 5

<Evaluation of Water Culture of Tomato Seedlings>

Seeds of tomato "Momotaro" were sown in a box, and seedlings having 3 true leaves at the expansion period were used. For the respective compositions, the test was repeated 3 times. OKF2 (made by Otsuka Chemical Co., Ltd.) was diluted (as N:P:K=260:149:247 (ppm)/OKF2 to be 538 times) as a NPK base and then resultant was added to a culturing solution. The present test was performed under conditions shown in Table 5. After 6 days from the start of the test, the culturing solution was sampled, and it was examined by means of RQ Flex (made by Merk) to obtain absorption efficency of nitrate nitrogen. The each value as relative value shows an absorption amount of nitrate nitrogen at each treatment in the case of making NPK culturing solution to be control. Also, at 6 days after starting of test, SPAD value (SPAD 502 made by Minolta Co., Ltd.) representing green degree of a leaf were measured. When the control (Comparative product 5-4) made up to be 100, the relative value is compared. The results are shown in Table 5. Then, fertilizer composition of OKF2 (Otsuka Chemical Co., Ltd.) was as follows: N:P:K:Ca:Mg=14:8:16:6:2.

TABLE 5

| Test No. | Blended raw materials | Concentration (ppm) | absorbing nitrogen | Efficiency of SPAD value |
|---|---|---|---|---|
| Invention product | | | | |
| 5-1 | Stearyl alcohol | 50 | 207 | 109 |
|  | POE(20) sorbitan monooleate | 150 |  |  |
|  | EDTA.4Na | 20 |  |  |
| 5-2 | Stearyl alcohol | 50 | 182 | 107 |
|  | POE(20) sorbitan monooleate | 150 |  |  |
| 5-3 | Stearyl alcohol | 50 | 175 | 106 |
|  | POE(20) sorbitan monooleate | 150 |  |  |
|  | Lauryl sulfuric acid sodium salt | 150 |  |  |
|  | EDTA.4Na | 20 |  |  |
| 5-4 | Stearyl alcohol | 50 | 170 | 105 |
|  | POE(20) sorbitan monooleate | 150 |  |  |
|  | Lauryl sulfuric acid sodium salt | 150 |  |  |
| 5-5 | Stearyl alcohol | 50 | 125 | 103 |
|  | Lauryl sulfuric acid sodium salt | 150 |  |  |
|  | EDTA.4Na | 20 |  |  |
| 5-6 | Lauryl alcohol | 50 | 134 | 104 |
|  | POE(20) sorbitan monooleate | 150 |  |  |
| 5-7 | Cetyl alcohol | 100 | 158 | 105 |
|  | POE(20) sorbitsn monooleate | 150 |  |  |
| 5-8 | Eicosanol | 50 | 162 | 104 |
|  | POE(20) sorbitan monooleate | 150 |  |  |
| 5-9 | Tetracosanol | 50 | 146 | 103 |
|  | POE(20)sorbitan monooleate | 150 |  |  |
| 5-10 | Lauryl alcohol | 50 | 128 | 102 |
|  | POE(20)sorbitan monooleate | 150 |  |  |
|  | Lauryl sulfuric acid sodium salt | 150 |  |  |
| 5-11 | Cetyl alcohol | 50 | 149 | 104 |
|  | POE(20)sorbitan monooleate | 150 |  |  |
|  | Lauryl sulfuric acid sodium salt | 150 |  |  |
| 5-12 | Eicosanol | 50 | 145 | 103 |
|  | POE(20) sorbitan monooleate | 150 |  |  |
|  | Lauryl sulfuric acid sodium salt | 150 |  |  |
| 5-13 | Tetracosanol | 50 | 135 | 101 |
|  | POE(20) sorbitan monooleate | 150 |  |  |
|  | Lauryl sulfuric acid sodium salt | 150 |  |  |
| Comparative product | | | | |
| 5-1 | Ethanol | 50 | 100 | 95 |
|  | POE(20) sorbitan monooleate | 150 |  |  |
| 5-2 | Hexanol | 50 | 97 | 97 |
|  | POE(20) sorbitan monooleate | 150 |  |  |
| 5-3 | Decyl alcohol | 50 | 95 | 96 |
|  | POE(20) sorbitan monooleate | 150 |  |  |
| 5-4 | NPK culturing solution (control) | — | 100 | 100 |

Example 6

<Test of Soil-irrigating Treatment for Spinach: Leaf Vegetable>

Species: "Esper"

Form of cultivation: a pot (diameter: 18 cm) for cultivation

Used soil: Kureha Engei Baido (horticultural soil made by Kureha Chemical Industry Co., Ltd.)

(Fertilizer components; N:P:K=0.4:1.9:0.6 (g) per 1 kg of the soil)

Seeds of spinach "Esper" were directly sown on the soil. As the culturing soil, the horticultural soil (made by Kureha Chemical Industry Co., Ltd.) was used in an amount of 1.3 L (1.5kg) per 1 pot (diameter of 18 cm). The number of repetition was made up to 18 pots. After 12 days from the sowing, treatment was started. At the intervals of 7 days, raw materials shown in Tables 6 and 7 were used to irrigate the soil 5 times in a treating amount of 150 ml/18 cm pot. After 6 days from the 5th irrigating treatment, weights of the plant and the SPAD value were examined. When the no-treated area (Comparative product 6–5) made up to be 100, the relative value is compared. The results are shown in Tables 6 and 7. During the test period, fertilizer components such as nitrogen, phosphorous and potassium were not applied as additional fertilizer and the plant absorbed only nutrients contained in the soil. Then, composition ratio of NPK fertilizer as the additional fertilizer was follows: N:P:K:Mg= 17:9.5:18:3.5.

TABLE 6

| Test No. | Blended raw materials | Concentration (ppm) | Weight | SPAD value |
|---|---|---|---|---|
| | Invention product | | | |
| 6-1 | Stearyl alcohol<br>POE(20) sorbitan monooleic acid ester (RHEODOL TW-O120) | 50<br>150 | 125 | 115 |
| 6-2 | Stearyl alcohol<br>POE(6) sorbitan monooleic acid ester (RHEODOL TW-O106) | 50<br>150 | 121 | 115 |
| 6-3 | Stearyl alcohol<br>POE(20) sorbitan monostearic acid ester (RHEODOL TW-S120) | 50<br>150 | 125 | 112 |
| 6-4 | Stearyl alcohol<br>POE(20) sorbitan tristearic acid ester (RHEODOL TW-S320) | 50<br>150 | 122 | 110 |
| 6-5 | Stearyl alcohol<br>POE(20) sorbitan cocont oil fatty acid ester (RHEODOL TW-L120) | 50<br>150 | 123 | 114 |
| 6-6 | Stearyl alcohol<br>Sorbitan monostearic acid ester (RHEODOL SP-S10) | 50<br>150 | 122 | 112 |
| 6-7 | Stearyl alcohol<br>Sorbitan monooleic acid ester (RHEODOL SP-O10) | 50<br>150 | 123 | 113 |
| 6-8 | Stearyl alcohol<br>Sorbitan tristearic acid ester (RHEODOL SP-S30) | 50<br>150 | 122 | 112 |
| 6-9 | Stearyl alcohol<br>Sorbitan monopalmitic acid ester (RHEODOL SP-P10) | 50<br>150 | 121 | 110 |
| 6-10 | Stearyl alcohol<br>Sorbitan coconut oil fatty acid ester (RHEODOL SP-L10) | 50<br>150 | 122 | 112 |
| 6-11 | Stearyl alcohol<br>POE(30) sorbit tetraoleic acid ester (RHEODOL 430) | 50<br>150 | 121 | 112 |
| 6-12 | Stearyl alcohol<br>POE(40) sorbit tetraoleic acid ester (RHEODOL 440) | 50<br>150 | 123 | 114 |
| 6-13 | Stearyl alcohol<br>POE(60) sorbit tetraoleic acid ester (RHEODOL 460) | 50<br>150 | 122 | 113 |
| 6-14 | Stearyl alcohol<br>POE(140) monostearic acid polyethylene glycol (EMANON 3199) | 50<br>150 | 122 | 114 |
| 6-15 | Stearyl alcohol<br>POE(140) distearic acid polyethylene glycol (EMANON 3299) | 50<br>150 | 121 | 111 |

TABLE 6-continued

| Test No. | Blended raw materials | Concentration (ppm) | Weight | SPAD value |
|---|---|---|---|---|
| 6-16 | Stearyl alcohol<br>POE(40) hardened caster oil (EMANON CH-40) | 50<br>150 | 122 | 113 |
| 6-17 | Stearyl alcohol<br>POE(80) hardened caster oil (EMANON CH-80) | 50<br>150 | 121 | 113 |

In the case of the testing, each of agents is used after forced-emulsifing by a home-mixer.
Each of notes in parenthesis shows tradename made by Kao Corp.

TABLE 7

| Test No. | Blended raw materials | Concentration (ppm) | Weight | SPAD value |
|---|---|---|---|---|
| | Invention product | | | |
| 6-18 | $C_{16}/C_{18}$ alcohol ($C_{16}/C_{18}$ = 15/85)<br>Oleic acid potassium salt (OS-SOAP) | 50<br>150 | 120 | 112 |
| 6-19 | $C_{16}/C_{18}$ alcohol ($C_{16}/C_{18}$ 15/85)<br>Semi-hardened beef tallow fatty acid sodium salt S-SOAP) | 50<br>150 | 119 | 110 |
| 6-20 | $C_{16}/C_{18}$ alcohol ($C_{16}/C_{18}$ = 15/85)<br>Stearic acid sodium salt (SS-40N) | 50<br>150 | 118 | 110 |
| 6-21 | $C_{16}/C_{18}$ alcohol ($C_{16}/C_{18}$ = 15/85)<br>POE(4.5) lauryl ether acetic acid sodium salt (AKYPO RLM45NV) | 50<br>150 | 117 | 111 |
| 6-22 | $C_{16}/C_{18}$ alcohol ($C_{16}/C_{18}$ = 15/85)<br>POE(10) myristyl ether acetic acid sodium salt (AKYFO RLM100NV) | 50<br>150 | 116 | 111 |
| 6-23 | $C_{16}/C_{18}$ alcohol ($C_{16}/C_{18}$ = 15/85)<br>Lauryl phosohoric acid monoester sodium salt | 50<br>150 | 115 | 112 |
| 6-24 | $C_{16}/C_{18}$ alcohol ($C_{16}/C_{18}$ = 15/85)<br>Lauryl phosohoric acid diester sodium salt | 50<br>150 | 117 | 110 |
| 6-25 | $C_{16}/C_{18}$ alcohol ($C_{16}/C_{18}$ = 15/95)<br>POE(3) lauryl phosohoric acid monoester sodium salt | 50<br>150 | 118 | 110 |
| 6-26 | $C_{16}/C_{18}$ alcohol ($C_{16}/C_{18}$ = 15/85)<br>POE(4) lauryl ether (EMULGEN 104P) | 50<br>75 | 117 | 111 |
| 6-27 | $C_{16}/C_{18}$ alcohol ($C_{16}/C_{18}$ = 15/85)<br>POE(13) cetyl ether (EMULGEN 220) | 50<br>75 | 115 | 111 |
| 6-28 | $C_{16}/C_{18}$ alcohol ($C_{16}/C_{18}$ = 15/85)<br>POE(12) stearyl ether (EMULGEN 320P) | 50<br>75 | 115 | 113 |
| 6-29 | $C_{16}/C_{18}$ alcohol ($C_{16}/C_{18}$ = 15/85)<br>POE(9) octyl phenyl ether (EMULGEN 810) | 50<br>75 | 116 | 112 |

TABLE 7-continued

| Test No. | Blended raw materials | Concentration (ppm) | Result of the test Weight | SPAD value |
|---|---|---|---|---|
| 6-30 | $C_{16}/C_{18}$ alcohol ($C_{16}/C_{18}$ = 15/85) POE(9) nonyl phenyl ether (EMULGEN 909) | 50 75 | 114 | 110 |
| 6-31 | $C_{16}/C_{18}$ alcohol ($C_{16}/C_{18}$ = 15/85) POE(50) nonyl phenyl ether (EMULGEN 950) | 50 75 | 112 | 109 |
| 6-32 | $C_{16}/C_{18}$ alcohol ($C_{16}/C_{18}$ = 15/85) Alkyl glucoside (C10/C12/C14) (MYDOL 12) | 50 150 | 113 | 110 |
| 6-33 | $C_{16}/C_{18}$ alcohol ($C_{16}/C_{18}$ = 15/85) Alkyl glucoide (C9/C10/C11) (MYDOL 10) | 50 150 | 112 | 107 |
| 6-34 | $C_{16}/C_{18}$ alcohol ($C_{16}/C_{18}$ = 15/85) Lauryl diethyl amine oxide (AMPHITOL 20N) | 50 150 | 111 | 105 |
| 6-35 | $C_{16}/C_{18}$ alcohol ($C_{16}/C_{18}$ = 15/85) 2-alkyl-N-carboxy methyl-N-hydorxy ethyl imidazolium betaine | 50 150 | 111 | 110 |
| 6-36 | $C_{16}/C_{18}$ alcohol ($C_{16}/C_{18}$ = 15/85) Lauryl amido propyl betaine (AMPHITOL 20AB) | 50 150 | 110 | 110 |
| 6-37 | $C_{16}/C_{18}$ alcohol ($C_{16}/C_{18}$ = 15/85) Lauryl dimethyl amino acetic acid betaine (AMPHITOL 24B) | 50 150 | 109 | 107 |
| Comparative product | | | | |
| 6-1 | Decyl alcohol Lauryl sulfuric acid sodium salt (EMAL 0) | 50 150 | 75 | 80 |
| 6-2 | Hexacosanol Lauryl sulfuric acid sodium salt (EMAL 0) | 50 150 | 90 | 92 |
| 6-3 | Decyl alchohol POE(9) nonyl phenyl ether (EMULGEN 909) | 50 150 | 68 | 72 |
| 6-4 | Hexacosanol POE(9) nonyl phenyl ether (EMULGEN 909) | 50 150 | 85 | 87 |
| 6-5 | Water (no-treated area) | — | 100 | 100 |

In the case of the testing each of agents is used after forced-emulsifying by a home-mixer.
Each of notes in parenthesis shows tradename made by Kao Corp.

Example 7
<Test of Soil-treating for Rice-plant Seedlings: Treatment at the Raising Seedling Period>

Unhulled rice seeds (species of Koshihikari) were sown into a box (60×30 cm) for raising seedling. At the period transferring from the hardening period to the greening period after germination, treatment was started in an treating amount of 500 ml/the box for raising seedling. Raw materials shown in Table 8 were used to irrigate the soil 3 times into soil. After the 3 treatments, that is, after 15 days from the sowing, the heights and the weights of the seedlings and the SPAD value were examined. When the no-treated area (Comparative product 7–6) made up to be 100, the relative value is compared. The results are shown in Table 8. As basal fertilizer, N component was applied in an amount of 0.5 g per the box for raising seedling. During the test period, fertilizer components were not applied as additional fertilizer and rice-plant seedlings absorbed only nutrients contained in the soil.

TABLE 8

| Test No. | Blended raw materials | Concentration (ppm) | Height | Weight | SPAD value |
|---|---|---|---|---|---|
| Invention product | | | | | |
| 7-1 | Stearyl alcohol POE(20) sorbitan monooleate | 100 300 | 106 | 115 | 113 |
| 7-2 | Myristyl alcohol POE(20) sorbitan monooleate tartaric acid Na solt | 100 300 | 107 | 107 | 108 |
| 7-3 | Tetraosanol POE(20) sorbitan monooleate | 100 300 | 102 | 107 | 106 |
| 7-4 | Myristyl alchohol POE(20) sorbitan monooleate Oxamide | 100 300 50 | 106 | 108 | 110 |
| 7-5 | Lauryl alchohol POE(20) sorbitan monolaurate | 100 300 | 102 | 102 | 105 |
| 7-6 | Eicosanol POE(20) sorbitan monooleate | 100 300 | 104 | 110 | 109 |
| 7-7 | Oleyl alcohol POE(20) sorbitan monooleate EDTA.4Na | 100 300 50 | 108 | 119 | 116 |
| 7-8 | Stearyl alcohol Cetyl alcohol POE(20) sorbitan monooleate succucinic acid | 50 50 300 50 | 108 | 118 | 116 |
| 7-9 | Docosanol POE(20) sorbitan monooleate | 100 300 | 103 | 108 | 108 |
| 7-10 | Myristyl alcohol POE(20) sorbitan monooleate | 100 300 | 102 | 104 | 108 |
| 7-11 | Docasanol POE(20) sorbitan monooleate EDTA.4Na | 100 300 50 | 106 | 116 | 110 |
| 7-12 | Cetyl alcohol POE(20) sorbitan monooleate | 100 300 | 104 | 106 | 110 |
| 7-13 | Stearyl alcohol POE(20) sorbitan monooleate Malonic acid | 100 300 50 | 109 | 119 | 115 |
| 7-14 | Cetyl alcohol POE(20) sorbitan monooleate EDTA.4Na | 100 300 50 | 108 | 112 | 112 |
| 7-15 | Stearyl alcohol POE(20) sorbitan monooleate EDTA.4Na | 100 300 50 | 110 | 121 | 118 |
| 7-16 | Oleyl alcohol POE(20) sorbitan monooleate | 100 300 | 104 | 113 | 110 |
| 7-17 | Stearyl alcohol Cetyl alcohol POE(20) sorbitan monooleate | 50 50 300 | 104 | 109 | 112 |
| 7-18 | Tetraosanol POE(20) sorbitan monooleate gluconic acid | 100 300 50 | 104 | 110 | 109 |

TABLE 8-continued

| Test No. | Blended raw materials | Concentration (ppm) | Height | Weight | SPAD value |
|---|---|---|---|---|---|
| 7-19 | Eicosanol | 100 | 108 | 118 | 114 |
|  | POE(20) sorbitan monooleate | 300 |  |  |  |
|  | Ascorbic acid Na salt | 50 |  |  |  |
| 7-20 | Lauryl alcohol | 100 | 104 | 104 | 106 |
|  | POE(20) sorbitan monolaurate | 300 |  |  |  |
|  | Fumaric acid | 50 |  |  |  |
| Comparative product |  |  |  |  |  |
| 7-1 | Ethanol | 100 | 96 | 92 | 91 |
|  | POE(20) sorbitan monooleate | 300 |  |  |  |
| 7-2 | Ethanol | 100 | 97 | 96 | 95 |
|  | POE(20) sorbitan monooleate | 300 |  |  |  |
|  | Heptonic acid Na salt | 50 |  |  |  |
| 7-3 | Hexanol | 100 | 93 | 96 | 89 |
|  | POE(20) sorbitan monooleate | 300 |  |  |  |
|  | Malonic acid | 50 |  |  |  |
| 7-4 | Hexanol | 100 | 90 | 93 | 87 |
|  | POE(20) sorbitan monooleate | 300 |  |  |  |
| 7-5 | Octyl alcohol | 100 | 78 | 82 | 83 |
|  | POE(20) sorbitan monooleate | 300 |  |  |  |
| 7-6 | Water (non-treated area) | — | 100 | 100 | 100 |

What is claimed is:

1. A method of promoting plant growth, which consists essentially of treating a plant with a mono-alcohol having 12 to 24 carbon atoms as a plant growth agent.

2. A method of promoting plant growth, which consists essentially of treating a plant with a mono-alcohol having 12 to 24 carbon atoms as a plant growth agent and at least one compound selected from a surfactant, a fertilizer and a chelating agent.

3. The method according to claim 2, wherein said surfactant is selected from the group consisting of an ester group-containing nonionic surfactant, an ether group-containing nonionic surfactant having no nitrogen atom, an amphoteric surfactant, a carboxylic anionic surfactant and a phosphoric anionic surfactant.

4. A method of promoting plant growth, which consists essentially of treating a plant with
   a mono-alcohol having 12 to 24 carbon atoms as a plant growth agent,
   at least one compound selected from the group consisting of a surfactant, a fertilizer and a chelating agent, and
   at least one surfactant selected from an ester group-containing non-ionic surfactant and an ether group-containing non-ionic surfactant having no nitrogen atom.

5. A composition for promoting plant growth consisting essentially of
   a mono-alcohol having 12 to 24 carbon atoms, and
   one member selected from the group consisting of (i) a chelating agent, (ii) a surfactant and a chelating agent, (iii) a fertilizer and a chelating agent and (iv) a surfactant, a fertilizer and a chelating agent.

6. The composition for promoting plant growth according to claim 5, wherein said surfactant is selected from an ester group-containing nonionic surfactant, an ether group-containing nonionic surfactant having no nitrogen atom, an amphoteric surfactant, a carboxylic anionic surfactant and a phosphoric anionic surfactant.

7. The composition for promoting plant growth according to claim 6, wherein said surfactant is the ester group-containing nonionic surfactant or the ether group-containing nonionic surfactant having no nitrogen atom.

8. A composition for promoting plant growth consisting essentially of
   a mono-alcohol having 12 to 24 carbon atoms, and
   at least one surfactant selected from an ester group-containing nonionic surfactant, an ether group-containing nonionic surfactant having no nitrogen atom, an amphoteric surfactant, a carboxylic anionic surfactant and a phosphoric anionic surfactant.

9. The composition for promoting plant growth according to claim 8, wherein said surfactant is the ester group-containing nonionic surfactant or the ether group-containing nonionic surfactant having no nitrogen atom.

10. A composition for promoting plant growth consisting essentially of
    a mono-alcohol having 12 to 24 carbon atoms,
    a fertilizer, and
    at least one surfactant selected from an ester group-containing nonionic surfactant, an ether group-containing nonionic surfactant having no nitrogen atom, an amphoteric surfactant, a carboxylic anionic surfactant and a phosphoric anionic surfactant.

11. A method of treating a plant, which consists essentially of treating a plant directly with a mono-alcohol having 12 to 24 carbon atoms.

12. A method of treating a plant, which consists essentially of treating a plant with a mono-alcohol having 12 to 24 carbon atoms and at least one compound selected from a surfactant, a fertilizer and a chelating agent.

13. The method of treating a plant according to claim 12, wherein said surfactant is selected from the group consisting of an ester group-containing nonionic surfactant, an ether group-containing nonionic surfactant having no nitrogen atom, an amphoteric surfactant, a carboxylic anionic surfactant and a phosphoric anionic surfactant.

14. A method of treating a plant, which consists essentially of treating a plant directly with a mono-alcohol having 12 to 24 carbon atoms, wherein said mono-alcohol is a plant growth agent.

15. A method of promoting plant growth, which consists essentially of treating a plant directly with a mono-alcohol having 12 to 24 carbon atoms as a plant growth agent, and at least one surfactant selected from an ester group-containing non-ionic surfactant and an ether group-containing non-ionic surfactant having no nitrogen atom.

16. A method of promoting plant growth, which consists essentially of treating a plant with a mono-alcohol having 12 to 24 carbon atoms as a plant growth agent and at least one additive selected from a sugar, an amino acid, a vitamin, a plant growth regulator, an extract from seaweed and a fermentation extract of a microorganism.

17. A method of promoting plant growth, which consists essentially of treating a plant with a mono-alcohol having 12 to 24 carbon atoms as a plant growth agent and at least one compound selected from a surfactant, a fertilizer, a chelating agent, a sugar, an amino acid, a vitamin, a plant growth regulator, an extract from seaweed and a fermentation extract of a microorganism.

18. The method according to claim 17, wherein said surfactant is selected from the group consisting of an ester group-containing nonionic surfactant, an ether group-containing nonionic surfactant having no nitrogen atom, an amphoteric surfactant, a carboxylic anionic surfactant and a phosphoric anionic surfactant.

19. A method of promoting plant growth, which consists essentially of treating a plant with
   a mono-alcohol having 12 to 24 carbon atoms as a plant growth agent,
   at least one compound selected from a surfactant, a fertilizer, a chelating agent, a sugar, an amino acid, a vitamin, a plant growth regulator, an extract from seaweed and a fermentation extract of a microorganism, and
   at least one surfactant selected from an ester group-containing non-ionic surfactant and an ether group-containing non-ionic surfactant having no nitrogen atom.

20. A composition for promoting plant growth consisting essentially of
   a mono-alcohol having 12 to 24 carbon atoms,
   at least one additive selected from a sugar, an amino acid, a vitamin, a plant growth regulator, an extract from seaweed and a fermentation extract of a microorganism, and
   one member selected from the group consisting of (i) a chelating agent, (ii) a surfactant and a chelating agent, (iii) a fertilizer and a chelating agent and (iv) a surfactant, a fertilizer and a chelating agent.

21. The composition for promoting plant growth according to claim 20, wherein said surfactant is selected from the group consisting of an ester group-containing nonionic surfactant, an ether group-containing nonionic surfactant having no nitrogen atom, an amphoteric surfactant, a carboxylic anionic surfactant and a phosphoric anionic surfactant.

22. The composition for promoting plant growth according to claim 21, wherein said surfactant is the ester group-containing nonionic surfactant or the ether group-containing nonionic surfactant having no nitrogen atom.

23. A composition for promoting plant growth consisting essentially of
   a mono-alcohol having 12 to 24 carbon atoms,
   at least one additive selected from a sugar, an amino acid, a vitamin, a plant growth regulator, an extract from seaweed and a fermentation extract of a microorganism, and
   at least one surfactant selected from an ester group-containing nonionic surfactant, an ether group-containing nonionic surfactant having no nitrogen atom, an amphoteric surfactant, a carboxylic anionic surfactant and a phosphoric anionic surfactant.

24. The composition for promoting plant growth according to claim 23, wherein said surfactant is the ester group-containing nonionic surfactant or the ether group-containing nonionic surfactant having no nitrogen atom.

25. A composition for promoting plant growth consisting essentially of
   a mono-alcohol having 12 to 24 carbon atoms,
   a fertilizer,
   at least one additive selected from a sugar, an amino acid, a vitamin, a plant growth regulator, an extract from seaweed and a fermentation extract of a microorganism, and
   at least one surfactant selected from an ester group-containing nonionic surfactant, an ether group-containing nonionic surfactant having no nitrogen atom, an amphoteric surfactant, a carboxylic anionic surfactant and a phosphoric anionic surfactant.

26. A method of treating a plant, which consists essentially of treating a plant directly with a mono-alcohol having 12 to 24 carbon atoms, and at least one additive selected from a sugar, an amino acid, a vitamin, a plant growth regulator, an extract from seaweed and a fermentation extract of a microorganism.

27. A method of treating a plant, which consists essentially of treating a plant with a mono-alcohol having 12 to 24 carbon atoms and at least one compound selected from a surfactant, a fertilizer, a chelating agent, a sugar, an amino acid, a vitamin, a plant growth regulator, an extract from seaweed and a fermentation extract of a microorganism.

28. The method of treating the plant according to claim 27, wherein said surfactant is selected from the group consisting of an ester group-containing nonionic surfactant, an ether group-containing nonionic surfactant having no nitrogen atom, an amphoteric surfactant, a carboxylic anionic surfactant and a phosphoric anionic surfactant.

29. A method of treating a plant, which consists essentially of treating a plant directly with a mono-alcohol having 12 to 24 carbon atoms and at least one additive selected from a sugar, an amino acid, a vitamin, a plant growth regulator, an extract from seaweed and a fermentation extract of a microorganism, wherein said mono-alcohol is a plant growth agent.

30. A method of promoting plant growth, which consists essentially of treating a plant directly with a mono-alcohol having 12 to 24 carbon atoms as a plant growth agent, at least one additive selected from a sugar, an amino acid, a vitamin, a plant growth regulator, an extract from seaweed and a fermentation extract of a microorganism, and at least one surfactant selected from an ester group-containing nonionic surfactant and an ether group-containing non-ionic surfactant having no nitrogen atom.

* * * * *